(12) United States Patent
Asmussen et al.

(10) Patent No.: US 6,290,989 B1
(45) Date of Patent: Sep. 18, 2001

(54) EXPANDABLE GASTRO-RETENTIVE THERAPEUTIC SYSTEM WITH CONTROLLED ACTIVE SUBSTANCE RELEASE IN THE GASTRO-INTESTINAL TRACT

(75) Inventors: Bodo Asmussen, Bendorf; Karsten Cremer, Bonn; Hans-Rainer Hoffmann, Neuwied; Karin Ludwig, Neuwied; Michael Roreger, Neuwied, all of (DE)

(73) Assignee: LTS Lohmann Therapie-Systeme AG (DE)

( * ) Notice: Subject to any disclaimer, the term of this patent is extended or adjusted under 35 U.S.C. 154(b) by 0 days.

(21) Appl. No.: 09/341,492
(22) PCT Filed: Jan. 9, 1998
(86) PCT No.: PCT/EP98/00099
  § 371 Date: Aug. 31, 1999
  § 102(e) Date: Aug. 31, 1999
(87) PCT Pub. No.: WO98/31341
  PCT Pub. Date: Jul. 23, 1998

(30) Foreign Application Priority Data

Jan. 14, 1997 (DE) .............................. 197 00 915

(51) Int. Cl.⁷ .............................. A61K 9/32; A61K 9/54; A61K 9/26
(52) U.S. Cl. ........................... 424/473; 424/456; 424/484
(58) Field of Search .................................. 424/451, 456, 424/473, 457, 458, 484, 482

(56) References Cited

U.S. PATENT DOCUMENTS

| | | | |
|---|---|---|---|
| 4,207,890 | 6/1980 | Mamjek et al. | 128/223 |
| 4,849,246 | 7/1989 | Schmidt | 427/2 |
| 4,996,058 | 2/1991 | Sinnreich | 424/462 |
| 5,260,069 | 11/1993 | Chih-Ming | 424/451 |

FOREIGN PATENT DOCUMENTS

| | | |
|---|---|---|
| 34 00 106A | 11/1985 | (DE) . |
| 0 307 904A1 | 9/1988 | (EP) . |
| 0 338 383A | 10/1989 | (EP) . |
| 0 669 129A | 8/1995 | (EP) . |

*Primary Examiner*—James M. Spear
(74) *Attorney, Agent, or Firm*—D. Peter Hochberg; Katherine R. Vieyra; William H. Holt

(57) ABSTRACT

The present invention describes a device for the controlled release of active compounds in the gastrointestinal tract with delayed pyloric passage, having a component expandable on contact with gastric juice, which is surrounded by a polymer covering which is permeable to gastric juice and active compounds. The device contains at least one active compound which is present in a multiparticulate preparation which releases the active compound into the gastric juice with a delay. Compared with conventional pharmaceutical forms with delayed pyloric passage, the release of active compound from a device according to the invention can be better controlled; likewise the device can be easily rolled or folded and can be introduced into capsules without problems.

15 Claims, 1 Drawing Sheet

EXPANDABLE GASTRO-RETENTIVE THERAPEUTIC SYSTEM WITH CONTROLLED ACTIVE SUBSTANCE RELEASE IN THE GASTRO-INTESTINAL TRACT

This application is a 371 of PCT/EP98/00099 filed Jan. 9, 1998.

The invention relates to a device for the controlled release of active compounds in the gastrointestinal tract with delayed pyloric passage, having a component expanding on contact with gastric juice, which is surrounded by a polymer covering which is permeable to gastric juice and active compounds. It relates in particular to a device which, by means of the reversible expansion of a component contained in it, undergoes extension on contact with gastric juice, which delays the pyloric passage and thereby leads to a prolonged gastric residence time. U.S. Pat. No. 4,207,890 describes a device for the controlled release of active compounds, which by means of its expansion undergoes local retention in the stomach and thereby has a prolonged residence time in the same. The device has (a) a polymer covering, which is present in collapsed form before administration. The polymer covering itself has no openings and consists of a material which is virtually unhydratable, but is permeable to body fluids and active compounds. The device moreover has (b) an element which controls the release of active compound. According to Claim 2, this element can be the polymer covering itself. As a further element (c), the device has an expanding component on contact with body fluids.

Significant problems of the administration form remain unsolved, however. In particular, the patent specification gives no concrete advice on the preparation of the active compound or the manner of its introduction into the device. In the description of the invention (top of column 5), it is proposed to seal the active compound into a small sachet which in turn can be inserted into a capsule before it is incorporated into the device.

Such a solution is affected by serious disadvantages. In view of the fact that the entire device must be dimensioned such that it can still be administered orally, it is virtually impossible to accommodate in it an expandable element and a capsule which contains a sachet with active compound. The industrial production, filling and sealing of such a small sachet of active compound and its introduction into a small capsule could also be associated with great difficulties.

EP 0 307 904 A1 furthermore discloses a very specific embodiment of a gastroretentive device with an expanding component (a) which contains the active compound and whose expansion takes place by means of evolution of $CO_2$. A polymer covering (b) of polyvinyl alcohol in sachet form and (c) an additional covering decomposing in gastric juice, e.g. a capsule, are furthermore provided.

This EP 307 904 also offers no practical solution to the introduction of the active compound. According to the exemplary embodiments, active compound powder is introduced manually into the polyvinyl alcohol covering. It is particularly disadvantageous that active compound and—the alkaline—$CO_2$ generator are combined to give one element, although it is known that many active compounds are incompatible with alkaline auxiliaries, which even include some of those described in the patent specification as preferred (e.g. ASA).

Both EP 307 904 A1 and U.S. Pat. No. 4,207,890 lack advice on how the release rate is to be controlled independently of the permeability of the polymer covering provided, which is particularly important if a rapidly permeating active compound is to be administered over a relatively long time.

It is therefore the object of the present invention to create a gastroretentive pharmaceutical form having the advantages of an expandable device according to U.S. Pat. No. 4,207,890, but which is an improvement in the sense of the production technology, the active compound stability and the control of the active compound release rate independently of the properties of the integrity-preserving polymer covering.

This object is achieved in very general form by a device for the controlled release of active compounds in the gastrointestinal tract with delayed pyloric passage, having a component expandable on contact with gastric juice, which is surrounded by a polymer covering which is permeable to gastric juice and active compounds, and which contains at least one active compound in the form of a multiparticulate preparation which releases the active compound into the gastric juice with a delay. Particular features of the invention follow from the subclaims and from the description below.

A device according to the invention offers the possibility of controlling the release rate of the active compound or of the active compounds relatively independently of the permeability of the polymer covering by means of the nature and composition of the multiparticulate preparation. The polymer covering can thus be optimized with respect to other important properties such as strength, sealing ability, flexibility and permeability for gastric juice and must not be adjusted as a top priority to the control of the release rate. The same polymer covering, for example, can thus be used for various products with different active compounds or different multiparticulate preparations of active compounds. Equally, the combined administration of two active compounds with differing permeabilities is made possible by means of a single device in that a multiparticulate preparation of each active compound having an appropriate release profile is provided in the same device.

The possibility of controlling the release rate, which is largely independent of the polymer covering, is therefore particularly of importance, since the requirement must be made of the same covering or membrane that on contact with gastric juice it very rapidly absorbs water or makes possible the diffusing-in of water, which must lead within a short time to the activation of the expansion mechanism of the device. An absorption and diffusion of water which is as rapid as possible, however, is accompanied by particularly high hydrophilicity and, as a rule, by a rapid diffusion of dissolved substances—properties which possibly counteract control of the active compound release by the membrane over a period of hours. Conversely, polymer membranes which release dissolved active compounds only slowly cannot [lacuna] water sufficiently rapidly into the device, so that in the case of a device having such a membrane the danger exists that it passes through the pylorus before its expansion mechanism could be activated. A multiparticulate preparation with controlled release of active compound accordingly makes possible a particularly advantageous and varied possibility of constructing expanding gastroretentive systems.

The advantage of the better control of the release rate is combined in a device according to the invention with the advantage of the better introduction of active compound during preparation and the better handling ability of the device after the introduction of the active compound. In particular, the possibility of rolling, folding or compressing the device for the purpose of introduction into hard gelatine capsules is thus guaranteed. The spatial separation of active compound and expansion-promoting propellants in the device is also advantageous, since it lowers the danger of incompatibilities.

Within the meaning of this invention, the concept of the multiparticulate preparation which releases the active compound into the gastric juice with a delay includes all multiparticulate delayed-release forms known in pharmaceutical technology. In this case, these are preparation forms in which a large number of particles in each case define one dose unit of the active compound and in which the delayed-release mechanism is combined with the construction or the formulation of the individual particles. Preparations of this type can have, for example, the form of pellets, powders, granules, microcapsules, nanoparticles, etc. with particle sizes of below 3 mm in diameter; particle sizes of up to 2 mm in diameter are preferred. The delaying of the active compound release can be effected by covering the individual particles with a polymer film or with a fatty or waxy substance or by embedding the active compound in a suitable carrier material which does not disintegrate rapidly in gastric juice. Suitable carrier materials therefore as a rule contain auxiliaries which are lipophilic and poorly and/or slowly soluble.

A device with active compound which is present in a multiparticulate preparation whose individual particles have a coating controlling the release of active compound or which contains the active compound embedded in matrix form in a material controlling the release can be constructed, for example, as in the attached figures:

BRIEF DESCRIPTION OF THE DRAWINGS

Inside the polymer covering 1 of FIG. 1, which is permeable to gastric juice and dissolved active compound is a supply 2 of an expandable component and an amount 3 having a majority of particles which consist of active compound and a release-delaying material 5, the active compound 4 being embedded in this material 5 as in FIG. 2 or covered by this as in FIG. 3.

Alternatively, the multiparticulate preparation 3 of the active compound can itself be embedded in the material shaped as a polymer covering 1, as in FIG.4. This suggests itself if the dose of the active compound and, as a result of this, the amount of the preparation per device is low, for example the dose below about 10 mg and the amount of the preparation below about 30 mg, and if at the same time particular measures for the spatial separation of propellants and active compound preparation are necessary.

Figure 1:
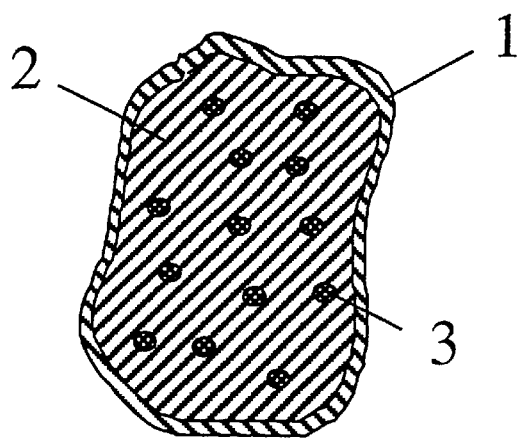
Figure 2:
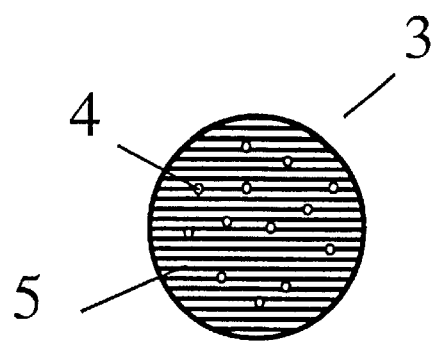
Figure 3:
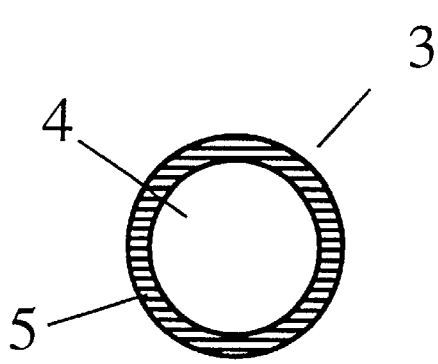
Figure 4:
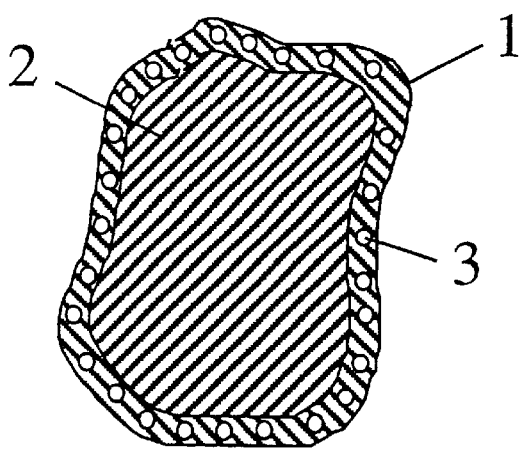

As in the case of other administration forms with controlled release of active compound, it can be desirable to bring a part of the active compound to act rapidly as an initial dose and to release the remaining part of the active compound in controlled form over a relatively long time to maintain the action. This can be achieved according to the invention by the amount of active compound which is to serve as an initial dose being present in the device as a rapid-release preparation, where the rapid-release preparation should be present in multiparticulate form in order to guarantee the unproblematical handling and further processing of the device. In the simplest case, a rapid-release preparation within the meaning of the invention can be a pure active compound powder. Frequently, however, it will be necessary to form and employ a preparation using customary pharmaceutical auxiliaries such as wetting agents, binding agents, flow-regulating agents, disintegration accelerators etc.

In order that a device according to the invention can be swallowed better and more pleasantly by patients, it is expedient that it is present in a further covering which rapidly disintegrates in the gastric juice. For this, according to the invention a hard gelatine capsule is preferred, which does not exclude the use of other coverings, e.g. starch capsules.

As the mechanism of expansion of the expandable component of the device, the generation of gas on contact with gastric juice is preferred. While various gases would be suitable from the physiological point of view, among them, for example, also nitrogen, nitrous oxide, methane and other gases, expansion with carbon dioxide is particularly preferred, since this can be released readily and in a relatively large amount from harmless propellants. In principle, suitable substances from which carbon dioxide can be released are various carbonates and hydrogen carbonates; on account of the good tolerability and the high yield a hydrogen carbonate, e.g. sodium hydrogen carbonate, is preferred according to the invention. A decision can be made here from case to case as to whether the release of carbon dioxide should take place solely due to the reaction of the hydrogen carbonate or of the carbonate with the acidic gastric juice, or whether the propellant itself should contain an acid component which can cause generation of gas on entry of water.

For the same reasons as explained above for the preparation of the active compound, a propellant according to the invention is also present as a multiparticulate preparation. It can also be necessary here to employ a part of the propellant or the entire amount as a delayed-release preparation, either as one whose individual particles have a covering controlling the release of gas or which contain a substance generating gas on contact with gastric juice embedded in matrix form in lipophilic, poorly or slowly soluble or slowly erodible material. The same pharmaceutical principles and auxiliaries as are employed in the delaying of the release of active compound can come to bear in the control of the release of carbon dioxide. For rapid expansion after the entry of gastric juice, the device can in some cases also contain a preparation of the propellant having rapid release of carbon dioxide. In the simplest case, a rapid-release preparation consists of a substance which releases carbon dioxide on reaction with gastric juice. Otherwise, it is a preparation formed using customary pharmaceutical auxiliaries.

The polymer covering of the device is formed from a material based on a hydrophilic polymer. The hydrophilicity of the polymer must be sufficient in order to make possible an absorption of water and a diffusion of water and of dissolved substances. At the same time, it is indispensable for the function of the device that the polymer covering or polymer membrane is insoluble in the gastric juice at body temperature, i.e. at temperatures of up to approximately 40° C. Many polymers having adequate hydrophilicity are therefore unsuitable, since in the majority they are perfectly soluble under the conditions indicated. Suitable polymers are, inter alia, those which are indeed hydrophilic due to a large number of appropriate functional groups, but at the same time have a crystalline, partially crystalline or crosslinked structure, such as, for example, various polyurethanes or highly hydrolysed polyvinyl alcohols.

For the optimum adjustment of the necessary mechanical and physicochemical properties of the polymer membrane such as strength, sealing ability, flexibility, hydrophilicity etc., in addition to the required polymer this can also additionally contain a further, modifying polymer or further, customary auxiliaries. Examples of auxiliaries which may be necessary are plasticizers, wetting agents, delustring agents, stabilizers, antioxidants, colorants. Specialists are able, from these and other customary auxiliaries, to select those necessary in nature and amount.

A further variant according to the invention of the polymer covering has a multilayer structure. Such a structure can be required by the fact that the combination of the necessary properties can be better realized in two layers of different composition; on the other hand, it may be advantageous or even necessary for reasons of production technology to construct the polymer covering from several layers.

In the individual case, it may also be necessary or practicable that the polymer covering is regionally different in structure or composition. For example, a sachet-like polymer covering can be imagined which is sealed together from two different polymer membranes, one polymer membrane having some of the necessary properties, the other having the other properties. For example, the permeability of the membrane for gastric juice and dissolved active compounds thus does not have to be equally good in all regions; on the other hand, a thin, mechanically stable, inexpensive membrane can also be used in this way if it is combined with another.

The device itself can be varied, if needed, in its structure such that it not only contains a compartment in which both the expandable component and the preparation of the active compound or of the active compounds are contained. In the embodiment according to the invention with several compartments, for example for the spatial separation of incompatible preparations, it is only to be required that at least one of the compartments contains an expandable component in order that a delay in the pyloric passage occurs.

Devices according to the invention can be employed therapeutically for various purposes. The three most important areas of use are the administration of active compounds for the local therapy of the stomach, the prolongation of the so-called invasion phase after oral administration of an active compound, and the administration of active compounds with so-called absorption windows in the stomach or in an upper section of the intestine.

The local therapy of the stomach, e.g. of the inflamed, eroded or infected gastric mucous membrane previously required the frequent administration of relatively high doses of active compound. This is accounted for in that on account of the short local duration of action of nonretentive administration forms the active compounds are frequently only brought to the site of action after systemic absorption and considerable dilution by means of the blood supply. Because of the long residence, the same active compound concentrations can be achieved immediately at or in the vicinity of the site of action by very much smaller doses by means of a gastroretentive device according to the invention. The dilution effect only comes to bear after the active compound has already passed through or infiltrated the site of action, so that in addition to the better efficacy an improved tolerability is also to be expected, since the active compound concentrations in the other body tissues are decreased.

The prolongation of the invasion phase is of interest and advantageous for all active compounds in which administration as a delayed-release preparation is useful in principle and of which an absorption in the distal sections of the intestine such as the large intestine is unknown or inadequate. This is true of the majority of the active compounds which are employed as delayed-release preparations. Usually, it is not possible to assume a reliable absorption of active compound beyond the small intestine, so that for the conception of conventional delayed-release forms the customary passage time of administration forms from administration up to leaving the small intestine—i.e. approximately 6–8 h—is taken as a basis. In this time, the active compound must be accordingly released and absorbed, so that even delayed-release preparations as a rule have to be taken at least twice a day. On account of their retention mechanism, which is activated in the stomach, devices according to the invention have a prolonged passage time up to leaving the small intestine, which is why they are suitable as delayed-release preparations having a longer release of active compound than 8 hours. In this way, it is possible to create administration forms which only have to be swallowed once daily or less frequently.

The necessary retention times of a device according to the invention are guaranteed, inter alia, by the nature, the composition and the adequate amount of the preparation of the gas-generating propellant, but also by the composition and the structure of the polymer membrane. For example, not only the amount of gas must be produced which is necessary for the expansion of the device, but moreover the amount which is lost to the outside by the diffusion of the gas through the membrane. If a device which has a volume of 4 $cm^3$ in the expanded state loses 2 $cm^3$ of gas per hour through its polymer covering, and if the expanded state is to be maintained for 15 hours, the preparation of the propellant must be able to generate at least 34 $cm^3$ of gas over a corresponding period of time.

Active compounds are moreover known which have an atypical absorption behaviour in the sense of a so-called absorption window. These active compounds are only absorbed into the body to an appreciable extent in a very short, tightly restricted area of the gastrointestinal tract. Riboflavin is an example of a substance which is only absorbed in an upper section of the small intestine. Conventional administration forms are less useful for administration of such substances; with delayed-release forms, in particular, large bioavailability deficits are seen which arise from the fact that the pharmaceutical form has already passed through the absorption window when a large part of the active compound has still not been released. Devices according to the invention are also highly suitable for these active compounds, since they deliver active compound solution over a relatively long period of time from an upper position in the gastrointestinal tract; a transit of undissolved active compound past the absorption window can be excluded.

The device according to the invention is furthermore suitable for the administration of those active compounds which have a comparatively low stability in the medium of the small and/or large intestine or which, due to the influence of substances or microorganisms occurring in the medium of the small and/or large intestine, suffer a reduced extent of bioavailability. An example of an active substance of this type is captopril, which on administration as a conventional delayed-release form is unstable in the intestine, and its bioavailability is greatly reduced by such an administration.

The use of the device for reducing the appetite or feeling of hunger is also suitable. In this case, the inhibition of appetite can be achieved in that the expanded device itself with appropriate size is recorded by the stomach mechanically just like supplied solid food and inhibits the feeling of hunger. In the same way or additionally, the inhibition can be caused by the release of an active compound having appetite-suppressant properties, which is given off from the device.

A device according to the invention can be produced as follows using a preparation process having several steps, where it is also possible from case to case for the person skilled in the art to carry out several of the described steps at the same time or to supplement or vary the process by additional steps customary in the production of medicaments, such as, for example, the coding of the individual devices:

In one process step, web-like material is prepared from which the polymer covering of the device is to be formed. In this case, it can be the same material or, as described above, webs of different material, if the device is to be constructed correspondingly. The web-like material is in this case brought together such that two layers of the material are located next to or on one another. When using the same material, this can be achieved by preparing the material as a single web and in this case folding it such that it is present in two layers.

In a further step, the superimposed layers are sealed with one another with application of heat and pressure in such a way that compartments are preformed, where the compartments must still not be completely sealed, but at least one unsealed site must remain for the filling of each compartment.

In a further step, the multiparticulate preparations of the active compound(s) and of the propellant are metered into each compartment. This can be achieved by means of aggregates, such as are customary for the metering of powders, granules or pellets, e.g. by means of screw feeders. Because of the possibly small size of the compartments, the aggregates must be modified under certain circumstances such that a particularly space-saving arrangement results. If preparations having particle sizes which are considerably different from one another have to be metered, e.g. powders and pellets, it may be necessary to use a metering unit for each preparation.

After the metering of the preparations into the compartments, the latter must be closed in a further process step by sealing. The individual devices can then be individualized in a further step by cutting or stamping. Alternatively, this step can be carried out at the same time as the sealing of the compartments by a combined sealing and stamping tool.

In a further process step, the devices thus obtained are brought into a form which is more compact and suitable for introduction into capsules by folding, rolling, compressing or other manipulations and filled into capsules, preferably into hard gelatine capsules.

What is claimed is:

1. Device for the controlled release of active compounds in the gastrointestinal tract with delayed pyloric passage comprising a component expandable on contact with gastric juice, a flexible polymer covering which is permeable to gastric juice and active compounds, wherein said polymer covering surrounds said expandable component and wherein said polymer covering contains at least one active compound present in a multiparticulate preparation consisting of individual particles containing said active compound, wherein said active compound is released into the gastric juice with a delay.

2. The device of claim 1 wherein at least some of the individual particles of the multiparticulate preparation have a coating controlling the release of active compound.

3. The device of claim 1 wherein the individual particles of the multipartculate preparation contain at least some of the active compound embedded in matrix form in lipophilic, poorly or slowly soluble or slowly erodible material.

4. The device of claim 1 wherein some of the active compound is present in a multiparticulate, rapid-release preparation.

5. The device of claim 1 wherein the multipartculate preparation is present partially or completely embedded in the polymer covering.

6. The device of claim 1 further comprising an additional covering which rapidly disintegrates in the gastric juice.

7. The device of claim 1 further comprising a second multiparticulate preparation which generates gas on contact with gastric juice.

8. The device of claim 7 wherein the particles of the second multipartculate preparation have a coating controlling the release of gas.

9. The device of claim 1 wherein the polymer covering is formed of one or more layers using a hydrophilic polymer which swells in aqueous liquids but is largely insoluble at temperatures up to 40° C.

10. The device of claim 1 wherein the construction or composition of the polymer is regionally different.

11. The device of claim 1 wherein the polymer covering is formed such that it forms several compartments, of which at least one is expandable.

12. The device of claim 1 which comprises at least one active compound which is effective against disorders of the stomach.

13. The device of claim 1 which comprises at least one active compound which is absorbed more rapidly and/or to a greater extent in the stomach or in the upper region of the small intestine than in the other sections of the gastrointestinal tract.

14. The device of claim 1 which comprises at least one active compound which has a comparatively low stability in the medium of the small and/or large intestine or, which due to the influence of substances or microorganisms occurring in the medium of the small and/or large intestine, can suffer a reduced extent of bioavailability.

15. Device for the controlled release of active compounds in the gastrointestinal tract with delayed pyloric passage comprising a component expandable on contact with gastric juice, a flexible polymer covering which is permeable to gastric juice and active compounds, wherein said polymer covering surrounds said expandable component and wherein said expandable component encloses at least one active compound present in a multiparticulate preparation consisting of individual particles containing said active compound, wherein said active compound is released into the gastric juice with a delay.

* * * * *